(12) United States Patent
Astier et al.

(10) Patent No.: US 10,557,779 B2
(45) Date of Patent: Feb. 11, 2020

(54) SEMICONDUCTOR MANUFACTURED NANO-STRUCTURES FOR MICROBE OR VIRUS TRAPPING OR DESTRUCTION

(71) Applicant: International Business Machines Corporation, Armonk, NY (US)

(72) Inventors: Yann Astier, Irvington, NY (US); David Esteban, Poughkeepsie, NY (US); Judson R. Holt, Wappingers Falls, NY (US); Henry K. Utomo, Newburgh, NY (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 256 days.

(21) Appl. No.: 15/142,175

(22) Filed: Apr. 29, 2016

(65) Prior Publication Data

US 2017/0191913 A1  Jul. 6, 2017

Related U.S. Application Data

(62) Division of application No. 14/988,887, filed on Jan. 6, 2016, now abandoned.

(51) Int. Cl.
| | | |
|---|---|---|
| C12M 3/00 | (2006.01) | |
| B01L 3/00 | (2006.01) | |
| G01N 1/40 | (2006.01) | |
| A61L 2/02 | (2006.01) | |
| C09D 5/16 | (2006.01) | |

(52) U.S. Cl.
CPC ............. *G01N 1/405* (2013.01); *A61L 2/02* (2013.01); *B01L 3/502707* (2013.01); *B01L 3/502761* (2013.01); *C09D 5/1681* (2013.01); *B01L 2200/0668* (2013.01);
(Continued)

(58) Field of Classification Search
CPC ..... C12M 35/04; C12M 35/00; B01L 3/5027; B01L 3/502753; B01L 3/502761
See application file for complete search history.

(56) References Cited

U.S. PATENT DOCUMENTS

| | | | |
|---|---|---|---|
| 5,635,358 A | 6/1997 | Wilding et al. | |
| 6,193,647 B1 * | 2/2001 | Beebe ............... | A61B 17/435 600/33 |

(Continued)

FOREIGN PATENT DOCUMENTS

| | | |
|---|---|---|
| KR | 20070099462 A | 10/2007 |
| WO | 2013046116 A1 | 4/2013 |

(Continued)

OTHER PUBLICATIONS

List of IBM Patents or Patent Applications Treated as Related; Date Filed: May 10, 2016; p. 1-2.

(Continued)

*Primary Examiner* — Nathan A Bowers
(74) *Attorney, Agent, or Firm* — Cantor Colburn LLP; Alvin Borromeo

(57) ABSTRACT

A device for isolating a microbe or a virion includes a semiconductor substrate; and a trench formed in the semiconductor substrate and extending from a surface of the semiconductor substrate to a region within the semiconductor substrate; wherein the trench has dimensions such that the microbe or the virion is trapped within the trench.

6 Claims, 22 Drawing Sheets

(52) U.S. Cl.
CPC ............... *B01L 2300/0816* (2013.01); *B01L 2300/0864* (2013.01); *B01L 2300/0893* (2013.01)

(56) References Cited

U.S. PATENT DOCUMENTS

| | | | |
|---|---|---|---|
| 6,616,327 B1* | 9/2003 | Kearney | B01F 5/06 366/340 |
| 6,653,124 B1* | 11/2003 | Freeman | B01L 3/5027 435/286.5 |
| 6,846,668 B1 | 1/2005 | Garman et al. | |
| 7,884,446 B2 | 2/2011 | Mazur et al. | |
| 7,927,651 B2 | 4/2011 | Hong et al. | |
| 8,062,596 B2 | 11/2011 | Yun et al. | |
| 8,492,714 B2 | 7/2013 | Reed et al. | |
| 8,709,791 B2 | 4/2014 | Larson et al. | |
| 8,947,657 B2 | 2/2015 | Letant et al. | |
| 8,960,582 B2 | 2/2015 | Kelson et al. | |
| 9,445,840 B2* | 9/2016 | Han | A61B 17/435 |
| 9,559,240 B1* | 1/2017 | Astier | H01L 31/125 |
| 10,246,730 B2 | 4/2019 | Astier et al. | |
| 2003/0148401 A1* | 8/2003 | Agrawal | B01J 19/0046 506/9 |
| 2004/0063100 A1 | 4/2004 | Wang | |
| 2007/0264705 A1* | 11/2007 | Dodgson | A61B 17/435 435/283.1 |
| 2008/0125743 A1 | 5/2008 | Yuzhakov | |
| 2009/0098541 A1 | 4/2009 | Southern | |
| 2009/0181450 A1 | 7/2009 | Ribault et al. | |
| 2010/0022416 A1 | 1/2010 | Flemming et al. | |
| 2011/0034860 A1 | 2/2011 | Melsheimer | |
| 2011/0262307 A1 | 10/2011 | Packirisamy et al. | |
| 2011/0272789 A1* | 11/2011 | Wang | B01L 3/502707 257/618 |
| 2012/0094382 A1 | 4/2012 | Park et al. | |
| 2012/0256027 A1 | 10/2012 | Yang et al. | |
| 2012/0264108 A1 | 10/2012 | Chen | |
| 2013/0109585 A1 | 5/2013 | Haynes et al. | |
| 2014/0056947 A1 | 2/2014 | Adelung et al. | |
| 2014/0249042 A1 | 9/2014 | Larson et al. | |
| 2014/0349892 A1 | 11/2014 | Van Der Zaag et al. | |
| 2014/0357529 A1 | 12/2014 | Choi et al. | |
| 2015/0041316 A1 | 2/2015 | Miki et al. | |
| 2015/0299729 A1 | 10/2015 | Ballas et al. | |
| 2016/0049467 A1* | 2/2016 | Wu | H01L 29/66795 257/401 |
| 2017/0189570 A1 | 7/2017 | Astier et al. | |
| 2017/0191912 A1 | 7/2017 | Astier et al. | |
| 2017/0191913 A1 | 7/2017 | Astier et al. | |
| 2018/0108656 A1* | 4/2018 | Lin | H01L 27/0886 |

FOREIGN PATENT DOCUMENTS

| | | |
|---|---|---|
| WO | 2013095303 A1 | 6/2013 |
| WO | 2014193481 A1 | 12/2014 |
| WO | 2015072186 A1 | 5/2015 |

OTHER PUBLICATIONS

Yann Astier, "Semiconductor Manufactured Nano-Structures for Microbe or Virus Trapping or Destruction", U.S. Appl. No. 15/142,188, filed Apr. 29, 2016.

Yann Astier, "Semiconductor Manufactured Nano-Structures for Microbe or Virus Trapping or Destruction"; U.S. Appl. No. 14/988,861, filed Jan. 6, 2016.

Yann Astier, "Semiconductor Manufactured Nano-Structures for Microbe or Virus Trapping or Destruction"; U.S. Appl. No. 14/988,887, filed Jan. 6, 2016.

Akst, Jef; "Next Generation: Bactericidal Surface"; The Scientist Magazine; p. 1-4; retrieved from http://www.the-scientist.com/?articles.view/articleNo/38447/title/Next-Generation--Bactericidal-Surface/ on Dec. 21, 2015; 4 pages.

Das, N. et al.; "Reliability Study of Nanoporous Silicon Oxide Impedance Biosensor for Virus Detection: Influence of Surface Roughness"; IEEE Transactions on Device and Materials Reliability; p. 1-8; 2015.

S.W. Bedell, et al.; "Kerf-Less Removal of Si, GE, and III-V Layers by Controlled Spalling to Enable Low-Cost PV Technologies"; IEEE Journal of Photovoltaics; vol. 2, No. 2; p. 141-147.

List of IBM Patents or Patent Applications Treated as Related (Appendix P); Date Filed: Jul. 10, 2019; p. 1-2.

* cited by examiner

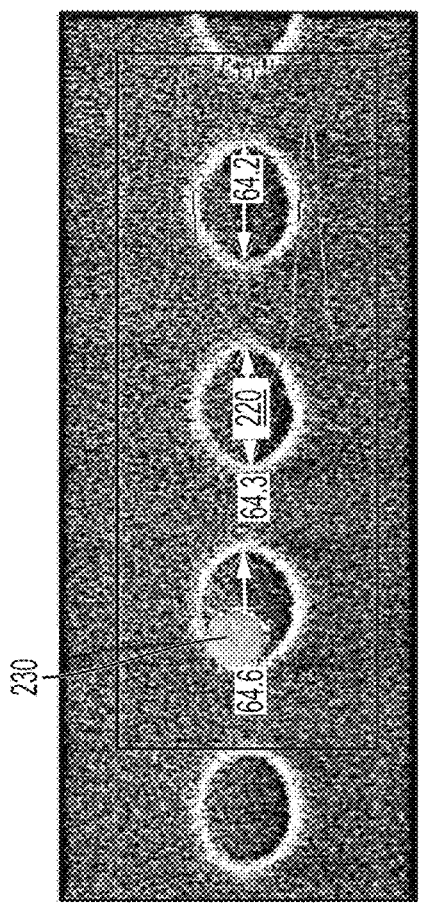
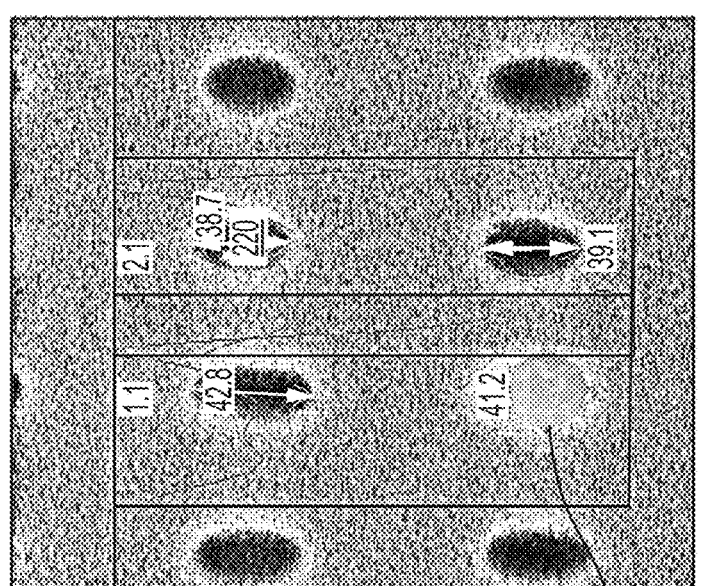
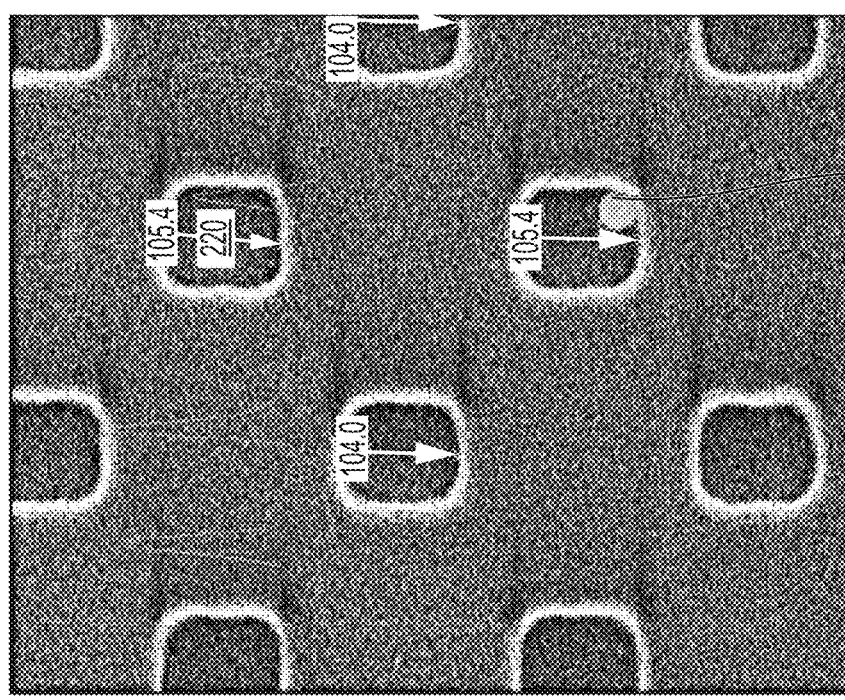
FIG. 2A
FIG. 2B
FIG. 2C

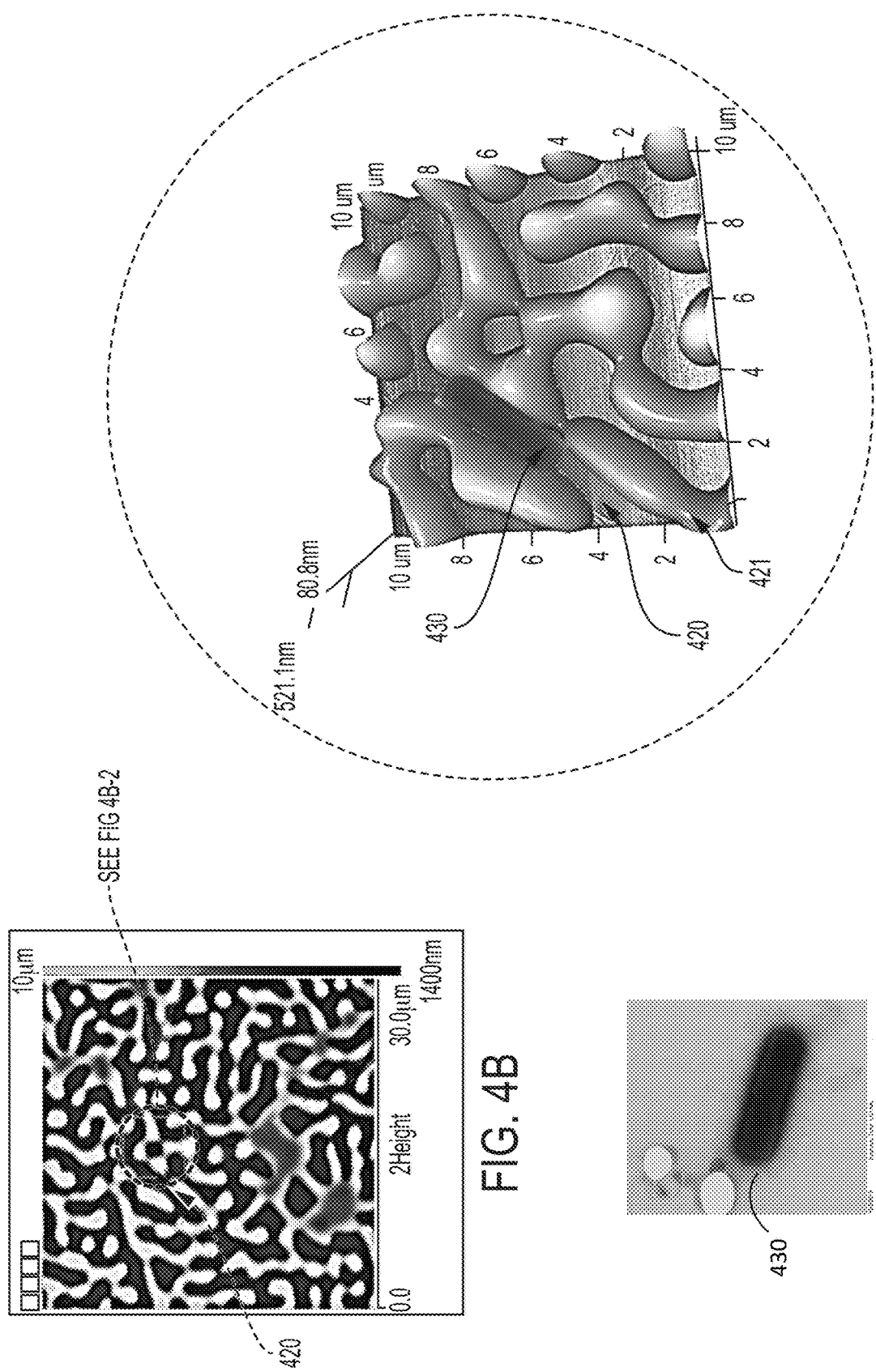

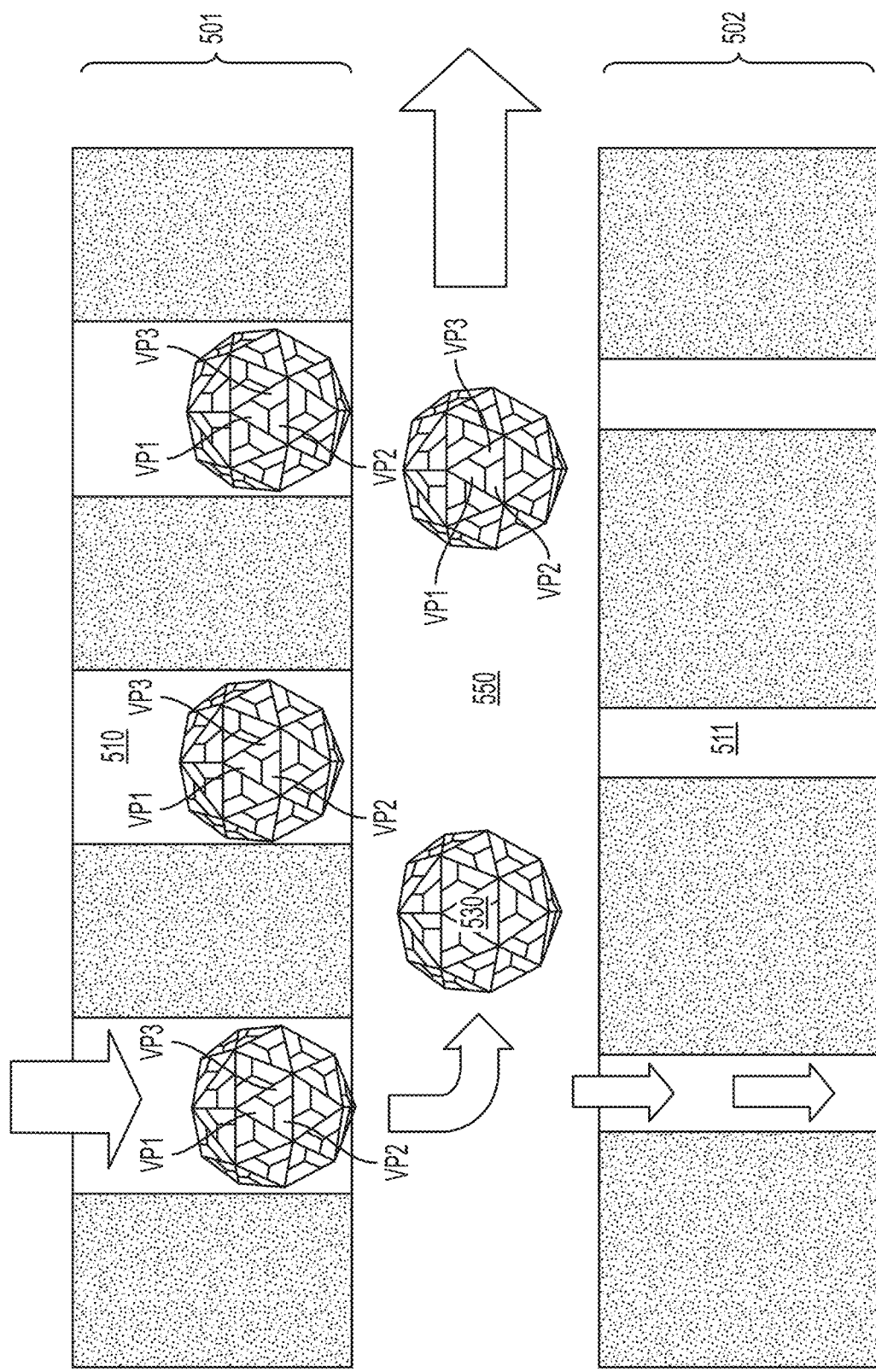

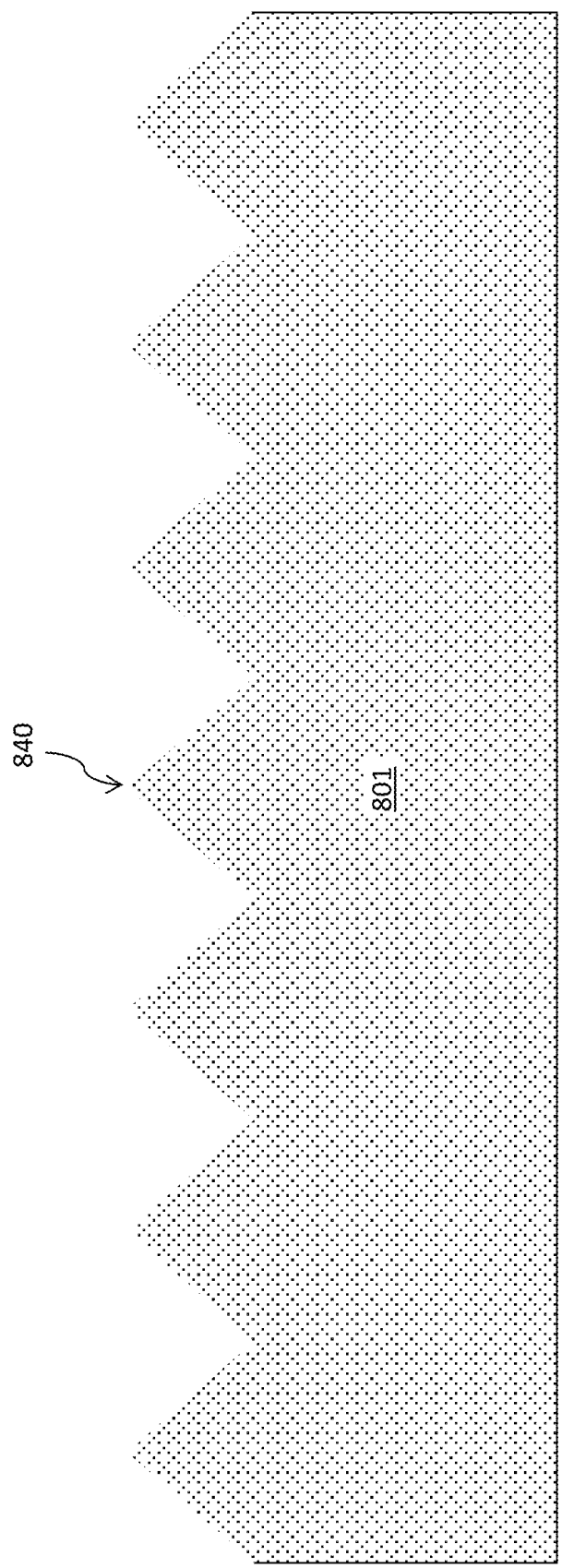

SEMICONDUCTOR MANUFACTURED NANO-STRUCTURES FOR MICROBE OR VIRUS TRAPPING OR DESTRUCTION

DOMESTIC PRIORITY

This application is a divisional of and claims priority to U.S. patent application Ser. No. 14/988,887, filed on Jan. 6, 2016, entitled "SEMICONDUCTOR MANUFACTURED NANO-STRUCTURES FOR MICROBE OR VIRUS TRAPPING OR DESTRUCTION", the entire contents of which are incorporated herein by reference.

BACKGROUND

The present invention relates to semiconductors, and more specifically, to semiconductor nanostructures.

Semiconductor materials have an electrical conductivity value that falls between that of a conductor, such as copper, and an insulator, such as glass. Semiconductor materials are used in many modern electronics. Semiconductor materials may be elemental materials or compound materials. Silicon, germanium, and alloys thereof, are two types of semiconductor materials used in many semiconductor devices.

Complementary metal oxide semiconductor (CMOS) technology is used for constructing integrated circuits. Semiconductor manufacturing techniques include various precise methods for forming nanoscale structures. CMOS technology is used in microprocessors, microcontrollers, static RAM, and other digital logic circuits. CMOS designs may use complementary and symmetrical pairs of p-type and n-type metal oxide semiconductor field effect transistors (MOSFETs) for logic functions.

SUMMARY

According to an embodiment, a device for isolating a microbe or a virion includes a semiconductor substrate; and a trench formed in the semiconductor substrate and extending from a surface of the semiconductor substrate to a region within the semiconductor substrate; wherein the trench has dimensions such that the microbe or the virion is trapped within the trench.

According to another embodiment, a device for isolating a microbe or a virion includes a first semiconductor layer having a first trench extending from a first surface to a second surface of the first semiconductor layer; a second semiconductor layer having a second trench extending from a first surface to a second surface of the second semiconductor layer, the second trench having a diameter that is smaller than the first trench; and an elongated gap positioned between portions of the first semiconductor layer and the second semiconductor layer.

Yet, according to another embodiment, a device for damaging or destroying a microbe or a virion includes a semiconductor substrate; and an array of protrusions having nanoscale dimensions extending from the semiconductor substrate; and wherein the microbe or the virion is damaged or destroyed after being disposed on the array of protrusions.

BRIEF DESCRIPTION OF THE DRAWINGS

The subject matter which is regarded as the invention is particularly pointed out and distinctly claimed in the claims at the conclusion of the specification. The foregoing and other features, and advantages of the invention are apparent from the following detailed description taken in conjunction with the accompanying drawings in which:

FIGS. 1-4B illustrate structures and methods of trapping microbes according to an embodiment embodiment, in which:

FIG. 1 illustrates a method for using holes (trenches) in a semiconductor substrate to trap a microbe/virion;

FIGS. 2A, 2B, and 2C illustrate patterned hole arrays of different dimensions;

FIGS. 4A, 4B and 4B-2 illustrate using a roughened nanosurface for trapping a microbe/virion, with FIG. 4B-2 being an expanded view of FIG. 4B;

FIG. 5 illustrates a method for size filtering microbes/virions according to another embodiment;

FIGS. 6A-9 illustrate methods of making nanoscale protrusions to damage/destroy a microbe/virion according to embodiments, in which:

FIGS. 6A, 6B, 6C, and 6D epitaxial growth on fins to create an array of nanospikes/needles;

FIGS. 8A-8E illustrate methods of making nanospikes, in which:

FIG. 8A is a cross-sectional side view of a photoresist and hard mask disposed on a substrate;

FIG. 8B is a cross-sectional side view after patterning the photoresist;

FIG. 8C is a top view of FIG. 8B;

FIG. 8D is a cross-sectional side view after rotating the substrate and performing a second patterning process;

FIG. 8E is a cross-sectional side view after recessing the substrate;

FIG. 8H is a cross-sectional side view after removing the remaining hard mask to form the array of nanospikes; and FIG. 9 illustrates a method for forming a flexible tube with an array of nanospikes.

DETAILED DESCRIPTION

Figure 1:
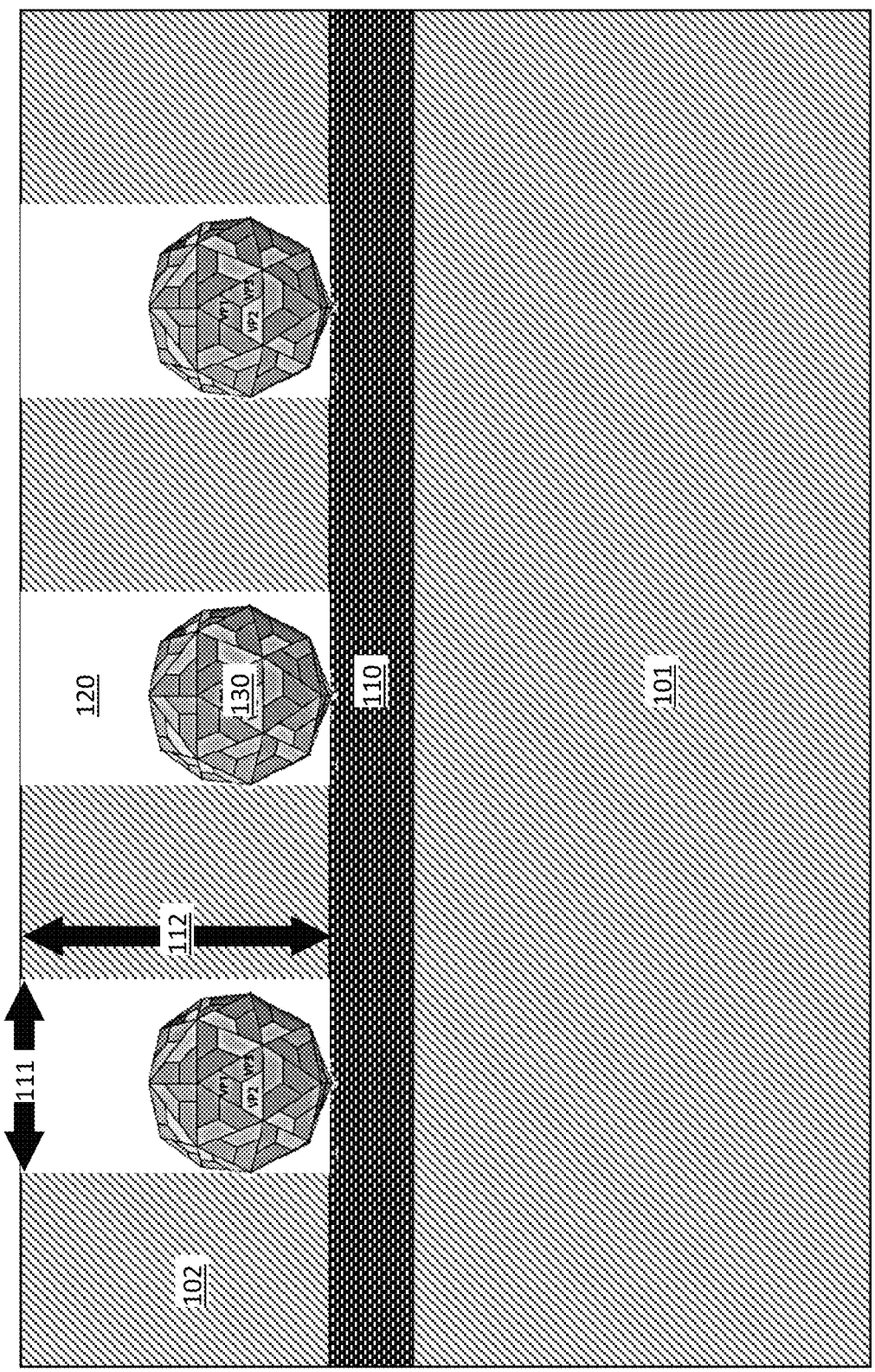

Semiconductor manufacturing techniques may be used to create precision-constructed nanostructures on the same scale as pathogenic organisms, for example, viruses and bacteria. By tuning the size and shape, the nanostructures may be used to trap, measure, physically filter, or attack and destroy the pathogens. Using such methods, the pathogens may not be prone to develop resistance.

Accordingly, various methods for trapping, measuring, filtering, and attacking pathogens are described herein. The disclosed methods reduce the risk for pathogens developing antibiotic resistance. In some embodiments, a size-based trapping/filtering mechanism is described. In other embodiments, a spike-like envelope puncture mechanism is used. Like reference numerals refer to like elements across different embodiments.

The following definitions and abbreviations are to be used for the interpretation of the claims and the specification. As used herein, the terms "comprises," "comprising," "includes," "including," "has," "having," "contains" or "containing," or any other variation thereof, are intended to cover a non-exclusive inclusion. For example, a composition, a mixture, process, method, article, or apparatus that comprises a list of elements is not necessarily limited to only those elements but can include other elements not expressly listed or inherent to such composition, mixture, process, method, article, or apparatus.

As used herein, the articles "a" and "an" preceding an element or component are intended to be nonrestrictive regarding the number of instances (i.e. occurrences) of the element or component. Therefore, "a" or "an" should be read to include one or at least one, and the singular word form of the element or component also includes the plural unless the number is obviously meant to be singular.

As used herein, the terms "invention" or "present invention" are non-limiting terms and not intended to refer to any single aspect of the particular invention but encompass all possible aspects as described in the specification and the claims.

As used herein, the term "about" modifying the quantity of an ingredient, component, or reactant of the invention employed refers to variation in the numerical quantity that can occur, for example, through typical measuring and liquid handling procedures used for making concentrates or solutions. Furthermore, variation can occur from inadvertent error in measuring procedures, differences in the manufacture, source, or purity of the ingredients employed to make the compositions or carry out the methods, and the like. In one aspect, the term "about" means within 10% of the reported numerical value. In another aspect, the term "about" means within 5% of the reported numerical value. Yet, in another aspect, the term "about" means within 10, 9, 8, 7, 6, 5, 4, 3, 2, or 1% of the reported numerical value.

As used herein, the term "microbe" means a microorganism, for example, a bacteria or an archaeon.

As used herein, the term "virion" means a viral DNA or RNA core with a protein coat, and optionally an external envelope.

Turning now to the Figures, FIGS. 1-4B illustrate structures and methods of trapping (isolating) microbes/virions according to an embodiment. FIG. 1 illustrates a method for using holes 120 (trenches) in a substrate 101 to trap a small microbe/virion 130. The substrate 101 may include a semiconductor material, a dielectric material, or any combination thereof. The size of the substrate 101 depends on the particular application and targeted microbe/virion 130.

Non-limiting examples of semiconductor materials include Si (silicon, including polysilicon), strained Si, SiC (silicon carbide), Ge (germanium), SiGe (silicon germanium), SiGeC (silicon-germanium-carbon), Si alloys, Ge alloys, III-V materials (e.g., GaAs (gallium arsenide), InAs (indium arsenide), InP (indium phosphide), aluminum arsenide (AlAs)), or any combination thereof. Other non-limiting examples of semiconductor silicon-on-insulator (SOI) substrates with buried oxide (BOX) layers.

Non-limiting examples of dielectric materials include dielectric oxides (e.g., silicon oxide), dielectric nitrides (e.g., silicon nitride), dielectric oxynitrides, or any combination thereof.

After forming the substrate 101, optionally, a microbe/virion binding material 110 is disposed on the substrate 101. The microbe/virion binding material 110 may be a material that has an affinity for the microbe/virion 130 of interest. In some embodiments (not shown), the microbe/virion binding material 110 may be disposed in the holes 120.

An additional layer 102 may be disposed on the substrate 101 to form the holes 120. Or the holes 120 (apertures/trenches) may be formed directly in the substrate 101. The additional layer 102 may be the substrate 101 material or another semiconductor and/or dielectric material.

The holes 120 may be formed in the substrate 101 or the additional layer 102 by performing lithography and etch process. The etch process may be a wet etch process or a dry etch process, for example, a reactive ion etch (RIE) process. The size of the holes 120, for example, the width 111 and depth 112, may generally vary and depend on the microbe/virion 130 that is targeted. For some microbes/virions 130, deeper trenches may more easily trap the target. The depths of the holes 120 may be, for example, up to 200 nm. The diameters of the holes 120 may become smaller (more narrow), as the depth increases.

The microbe/virion 130 may be for example, a bacterium, an archaeon, or other pathogen. The microbe/virion 130 will be trapped within the holes 120 after a solution or sample including the microbes/virions 130 is disposed on the surface of the semiconductor structures comprising the holes 120. The microbes/virions 130 then become trapped within the trenches.

The size of the holes 120 may generally vary and depend on the targeted microbe/virion. In some embodiments, the holes 120 have an average diameter in a range from about 70 to about 700 nm. In other embodiments, the holes 120 have an average diameter in a range from about 70 to about 150 nm.

In an exemplary embodiment, a 150 millimeter (mm) radius wafer may be used as the substrate. The 150 mm wafer has a surface area of about 0.0707 meters$^2$ (m$^2$), but only about half of the surface area may be sued to trap virions. An array of holes is formed in the substrate to trap a virus, for example, a poliovirus having about a 30 nm diameter. About 1.2e6 virions may be captured per wafer.

In another exemplary embodiment, the array of holes may be used as a virus strainer with a tuned pore size. Microelectronics processing methods may be used for precise channel size control.

In yet another exemplary embodiment, perpendicular double patterning may be used to form the holes. Deeper vertices and/or larger vertices within the substrate may allow virions to enter the substrate.

FIGS. 2A, 2B, and 2C illustrate patterned trench/hole arrays of different dimensions. FIG. 2A shows a microbe/virion 230 trapped within a hole 220 in a substrate having a diameter of about 105 nm. FIG. 2B shows a microbe/virion 230 trapped within a hole 220 having a diameter of about 64 nm. FIG. 2C shows a microbe/virion trapped within a hole 220 having a diameter of about 42 nm.

Figure 3B:
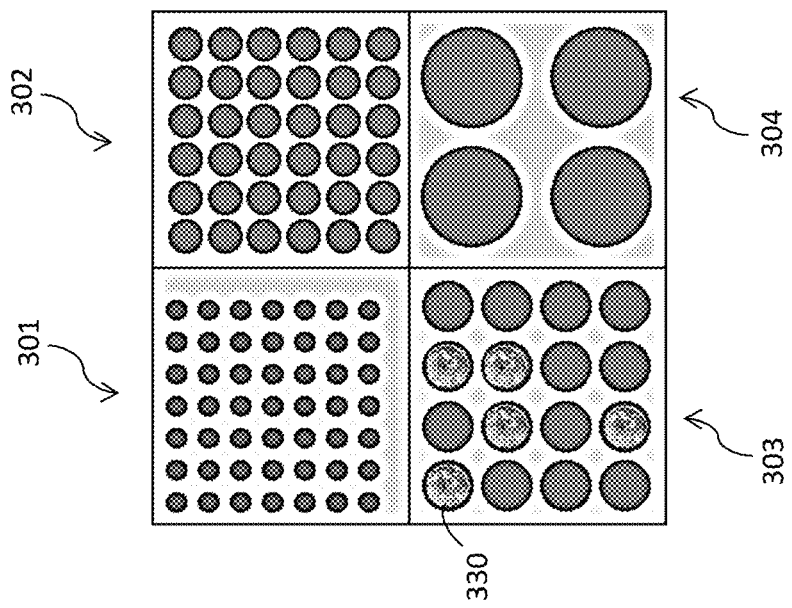
FIGS. 3A and 3B illustrate a method of using a patterned hole array to determine microbe/virion concentration.
Figure 3A:
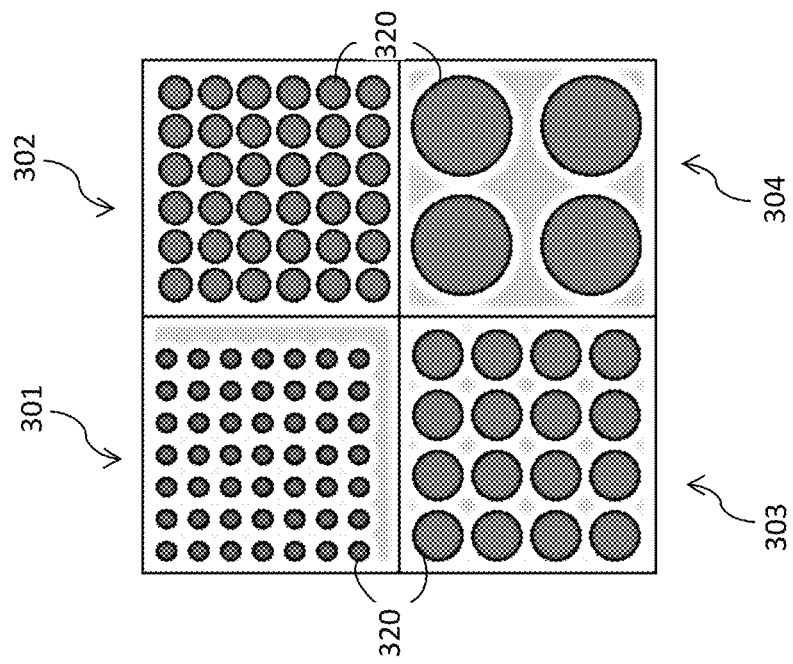

FIGS. 3A and 3B illustrate a method of using a patterned hole (trench) array to determine microbe/virion concentration. The patterned arrays may be used to quickly and easily determine microbe/virion concentrations. FIG. 3A shows arrays 301, 302, 303, 304 of holes 320 having different average sizes/diameters. A sample substrate/slide is prepared with various arrays of holes. The arrays 301, 302, 303, 304 are formed in different sections on a single substrate/slide.

Different sized holes formed on different parts of the substrate/slide may be used to study different sized microbes/virions 330.

The substrate/slide is exposed to an environment that includes microbes/virions 330 (e.g., using a solution including the microbe/virion), and the microbes/virions 330 are trapped within the holes 320, as shown in FIG. 3B. A solution may include different microbes and/or virions. The surface of the substrate/slide may be rinsed to remove excess particles.

The microbes/virions 330 may be labeled with a fluorescent marker so that a black box and camera may be used to record fluorescence intensity. The fluorescence intensity will be directly proportional to the labeled microbe/virion 330 concentration in the holes 320. If the concentration is too high (or at the maximum level of detection), a more dilute solution of the microbe/virion 330 may be used until a measurable concentration is achieved. The microbes/virions 330 also may be studies using other analytical methods. Using arrays of holes to conduct assays as described is fast, inexpensive, robust, and size selective.

FIGS. 4A and 4B illustrate using a roughened semiconductor nanosurface for trapping a microbe/virion 430. The roughened nanosurface shown in FIG. 4B may be formed by, for example, growing a high % germanium (Ge) epitaxial silicon germanium (SiGe) film on a silicon substrate. The SiGe film is annealed to form nanoscale Ge agglomerates 421. Elongated trenches 420 are formed between the Ge agglomerates 421 to form the roughened nanosurface. Optionally, the roughened nanosurface may be coated with an anti-microbial material, for example, copper.

The microbe/virion 430, shown in FIG. 4A, is trapped within the elongated trenches 420, as shown in FIG. 4B. The roughened nanosurface may be used to trap microbes/virions 430 with elongated shapes. The roughened nanosurface increases interactions between the substrate surface and the microbe/virion 430, which results in more microbes/virions 430 being trapped (or destroyed).

FIG. 5 illustrates a method for size filtering/isolating microbes/virions 530 according to another embodiment. Structures for size filtering may be formed using multiple semiconductor layers 501, 502 with different sized holes 510, 511. Multiple patterning and etching steps may be used to create holes 510, 511 and fluid gaps 550 (elongated gaps/trenches) between the layers 501, 502. Any number of layers and holes of any dimension may be used. The sequential layers may include different sized holes to filter out different sized microbes/virions 530.

A solution of the microbes/virions 530 is disposed on the first layer 501 of the semiconductor structure. The first layer 501 includes holes 510 with diameters that are larger than the holes 511 in the second layer 502. The solution may include different sized microbes/virions 530. Microbes/virions 530 are large enough to pass through the holes 510 in the first layer 501, but are too large to pass through the holes 511 in the second layer 502 will be filtered through the fluid gap 550 between the first and second layers 501, 502. The microbes/virions 530 will exit (be expelled) between the layers and can be collected. Purified fluid, or fluid with smaller microbes/virions that may pass through the holes in the next layer (holes 511), will travel through the second layer 502 and exit the holes 511 in the second layer 502. The semiconductor structure may include other layers beneath second layer 502, as well as a second fluid gap beneath second layer 502 so that other particles are expelled from a different output area in the structure.

According to another embodiment, spikes (protrusions) of nanometer sized dimensions (nanospikes or nanoneedles) may be used to damage/destroy microbes/virions according to a third embodiment, which is described in FIGS. 6A through 9 below. The size of the nanospikes (nanoprotrusions) may depend on the size of the targeted microbe/virion. A solution comprising the microbe/virion is disposed on a surface of the array of protrusions to damage/destroy the microbe/virion. The nanospikes may have any size/dimension, and for example, may have sharp/blunt ends.

Figure 6C:
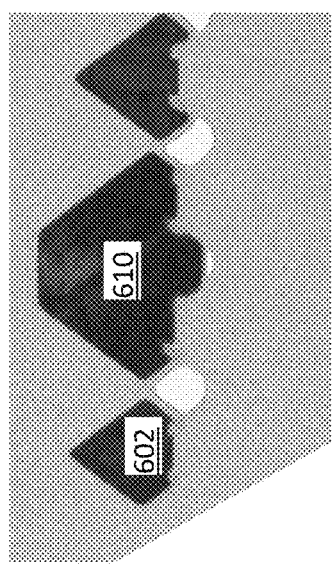
Figure 6D:
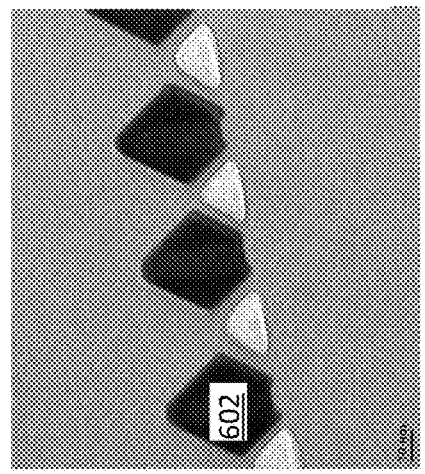
Figure 6A:
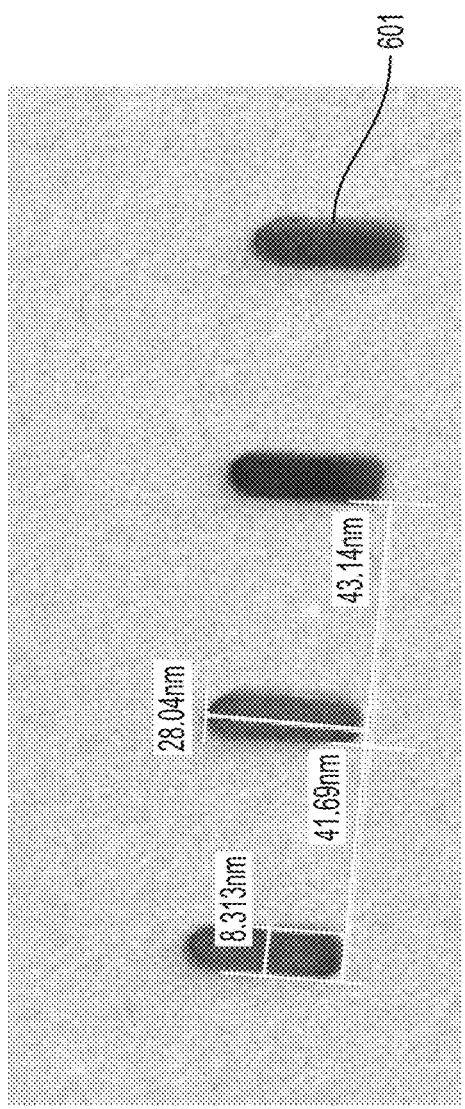
Figure 6B:
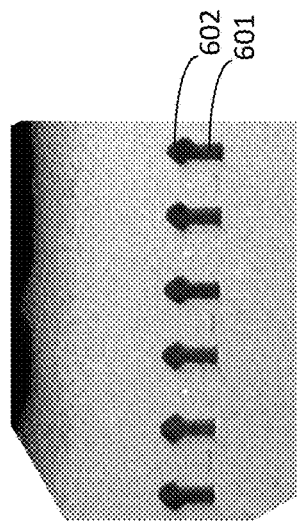

FIGS. 6A, 6B, 6C, and 6D show epitaxial growth on fins (protrusions) to create an array of nanospikes. The nanospikes may be formed by, for example, forming epitaxial growth on semiconductor fin structures (e.g., FinFET fins). As shown in FIG. 6A, fins 601 are patterned in a semiconductor substrate material. The epitaxial growth process may be, for example, chemical vapor deposition (CVD) (liquid phase (LP) or reduced pressure chemical vapor deposition (RPCVD), vapor-phase epitaxy (VPE), molecular-beam epitaxy (MBE), liquid-phase epitaxy (LPE), metal organic chemical vapor deposition (MOCVD), or other suitable processes. The epitaxial growth process creates a diamond-shaped epitaxial growth 602 on surfaces and sidewalls of the fins 601, as shown in FIGS. 6A, 6C, and 6D. The epitaxial growth process may be controlled to create spikes of different sizes, as shown in FIG. 6C. Larger nanospikes may be created by merging two adjacent epitaxial growths, as shown by the large merged epitaxial growth 610. Larger or smaller nanospikes may be formed, depending on the targeted microbe/virion.

The dimensions and density of the nanospikes is chosen based on the targeted microbe/virion size. The poliovirus has a diameter of about 30 nm. An *Escherichia coli* is about 0.5 micron×2 microns. A human cell is about 10-100 microns in size.

Figure 7A:
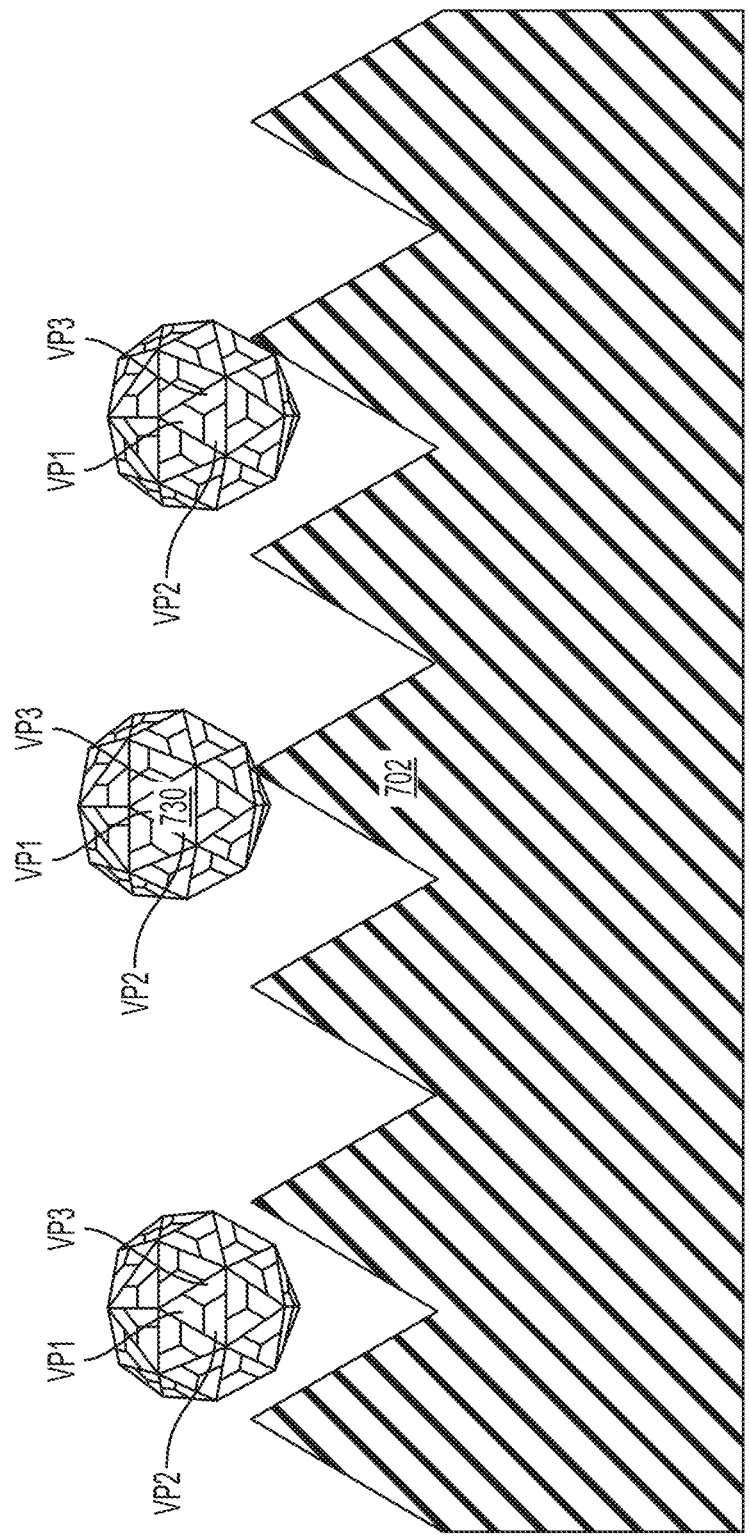
FIG. 7A illustrates a small dimension array of nanospikes.
Figure 7B:
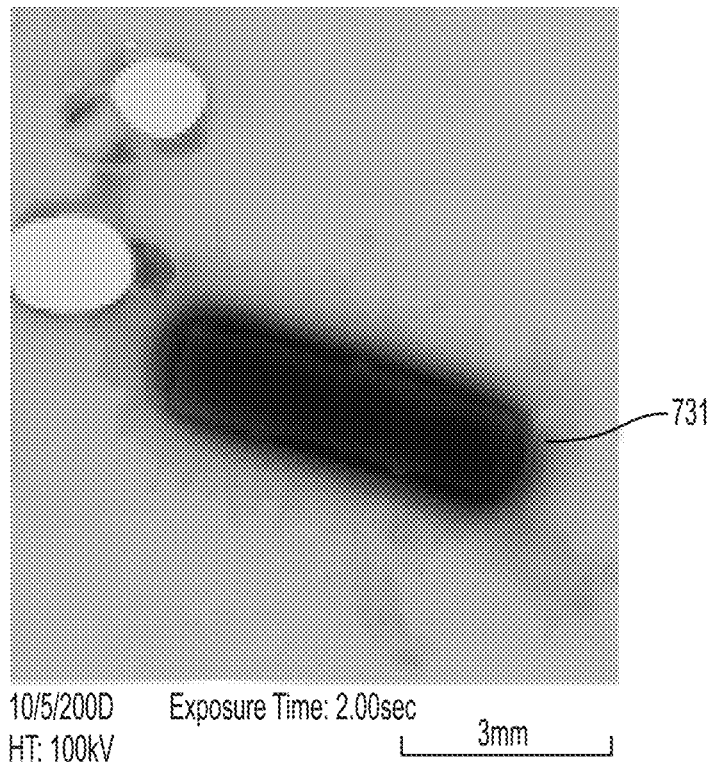
FIGS. 7B and 7C illustrate a large microbe/virion positioned on a small dimension array of nanospikes.
Figure 7C:
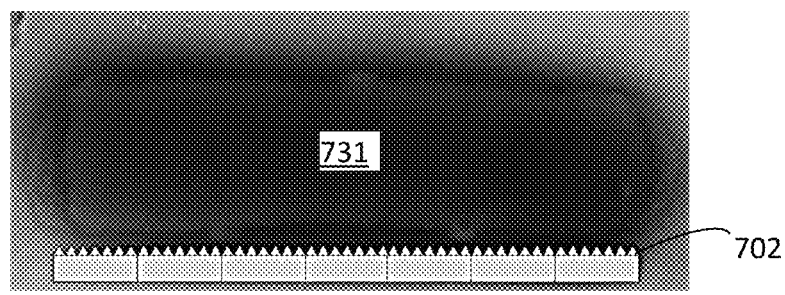
Figure 7D:
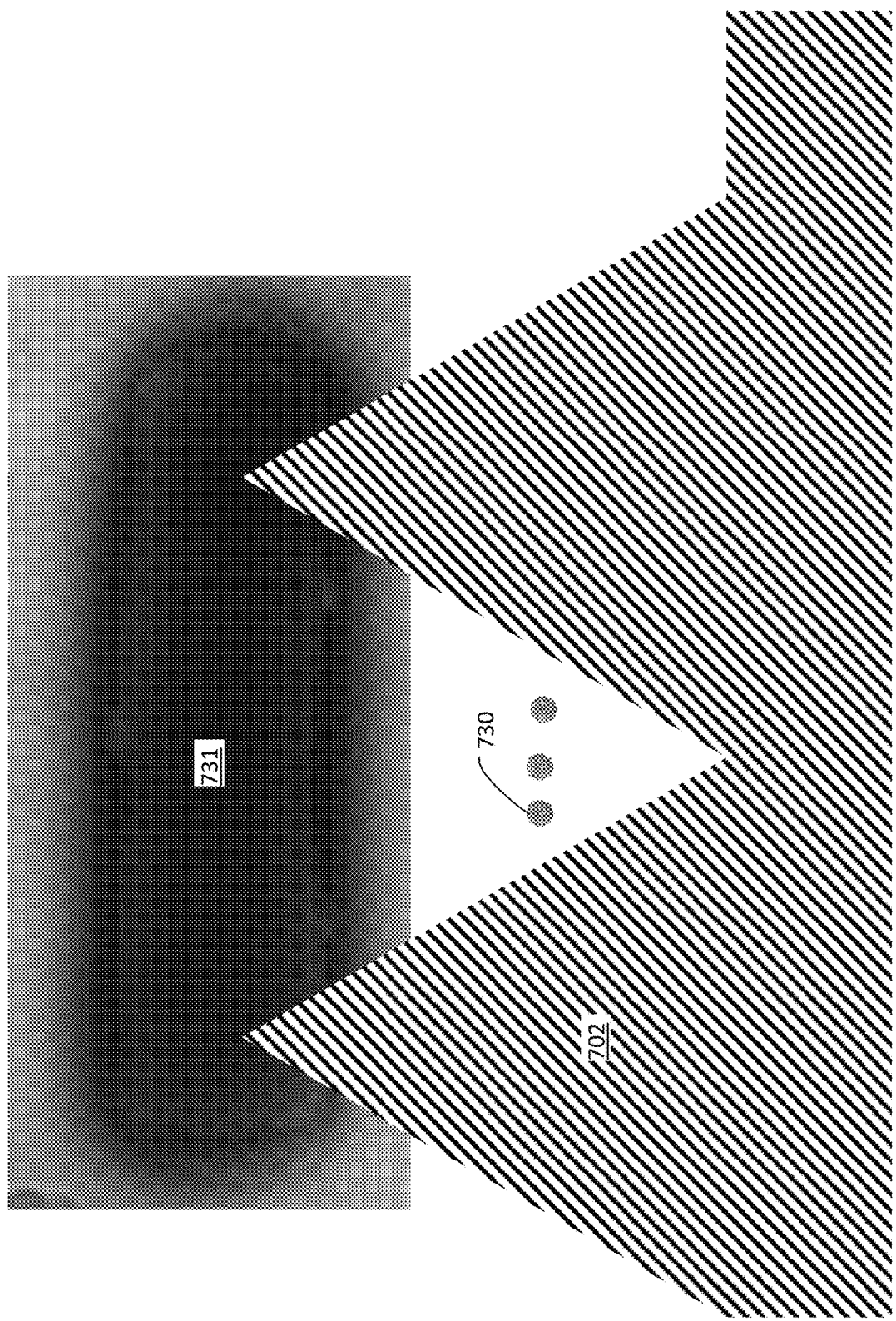
FIG. 7D is a large dimension array of nanospikes puncturing a large microbe/virion.

FIG. 7A illustrates an array of nanospikes 702 in which smaller microbes/virions 730 may be positioned between the individual nanospikes. FIGS. 7B and 7C illustrate a large microbe/virion 731 positioned on a small dimension array of nanospikes 702. The small dimension array of nanospikes 702 may not puncture a large microbe/virion 731 and may have a "bed of nails" effect. FIG. 7D is a large dimension array of nanospikes 702 puncturing a large microbe/virion 731. Smaller microbes/virions 730 are not punctured and fall between the nanospikes 702. Therefore, the nanospikes 702 only damage/destroy a specific size range of microbes/virions.

Figure 7E:
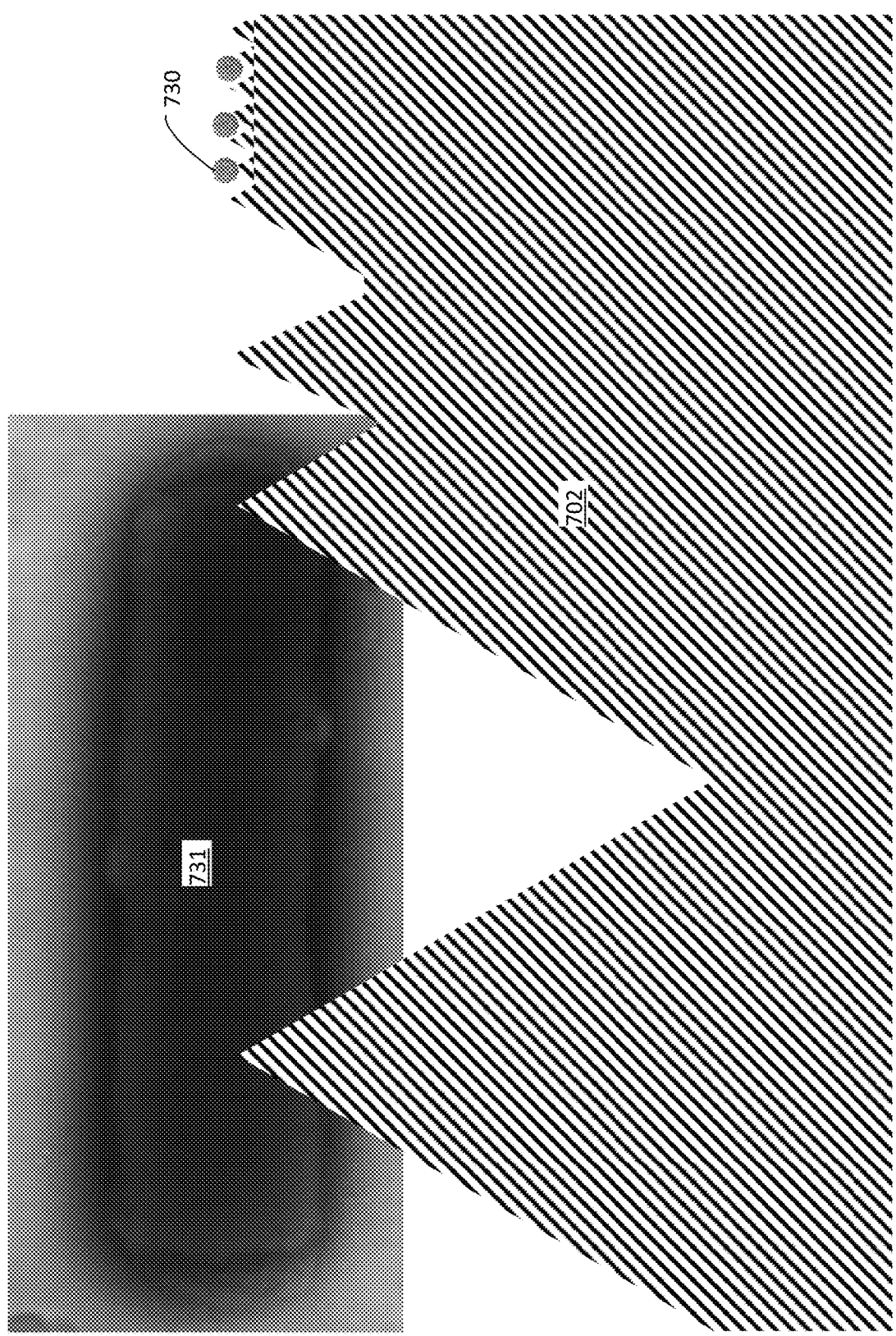
FIG. 7E is an array with nanospikes having different sizes.
Figure 7F:
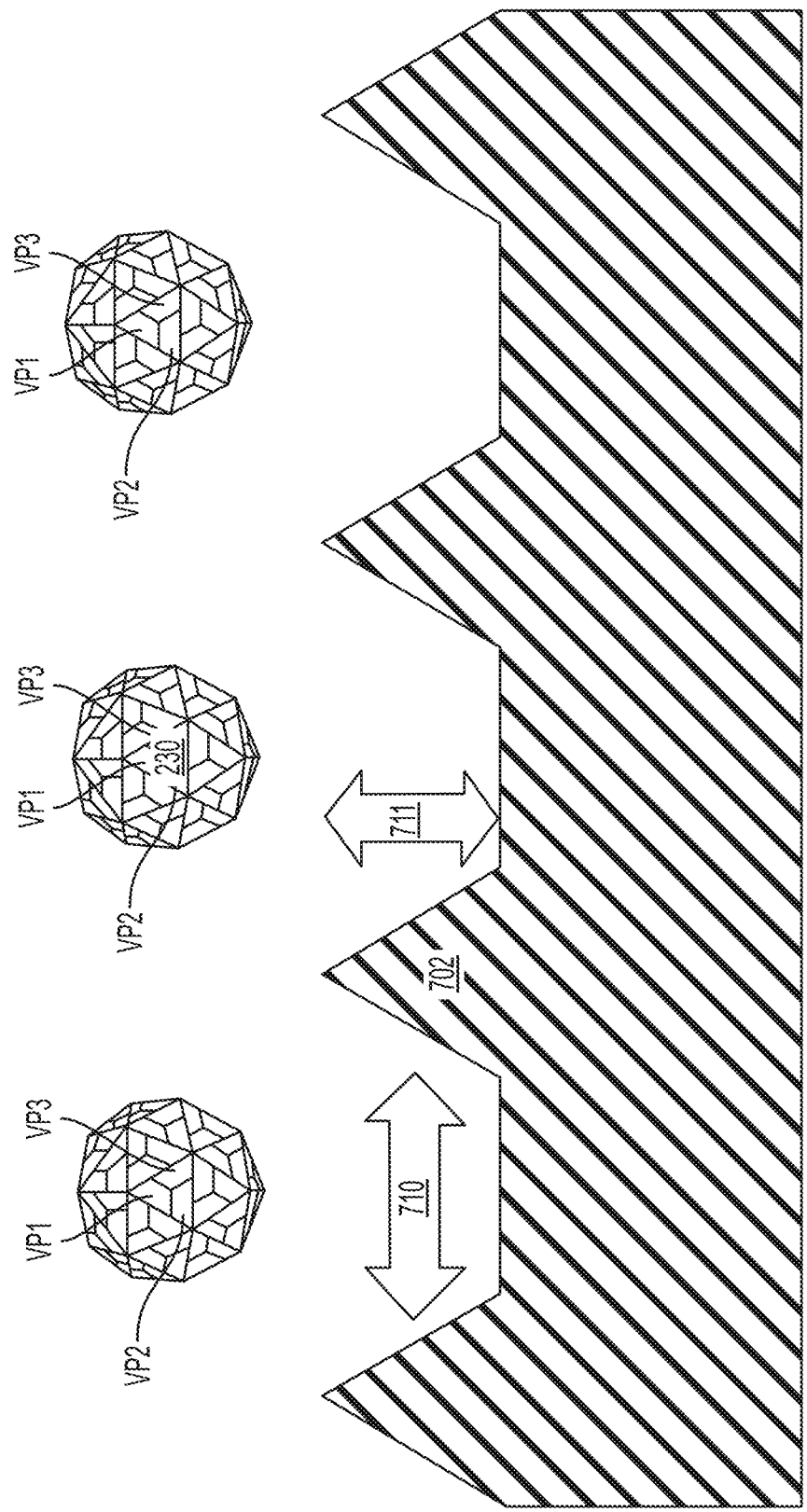
FIG. 7F is an array of nanospikes illustrating different spacing and depths.
Figure 7G:
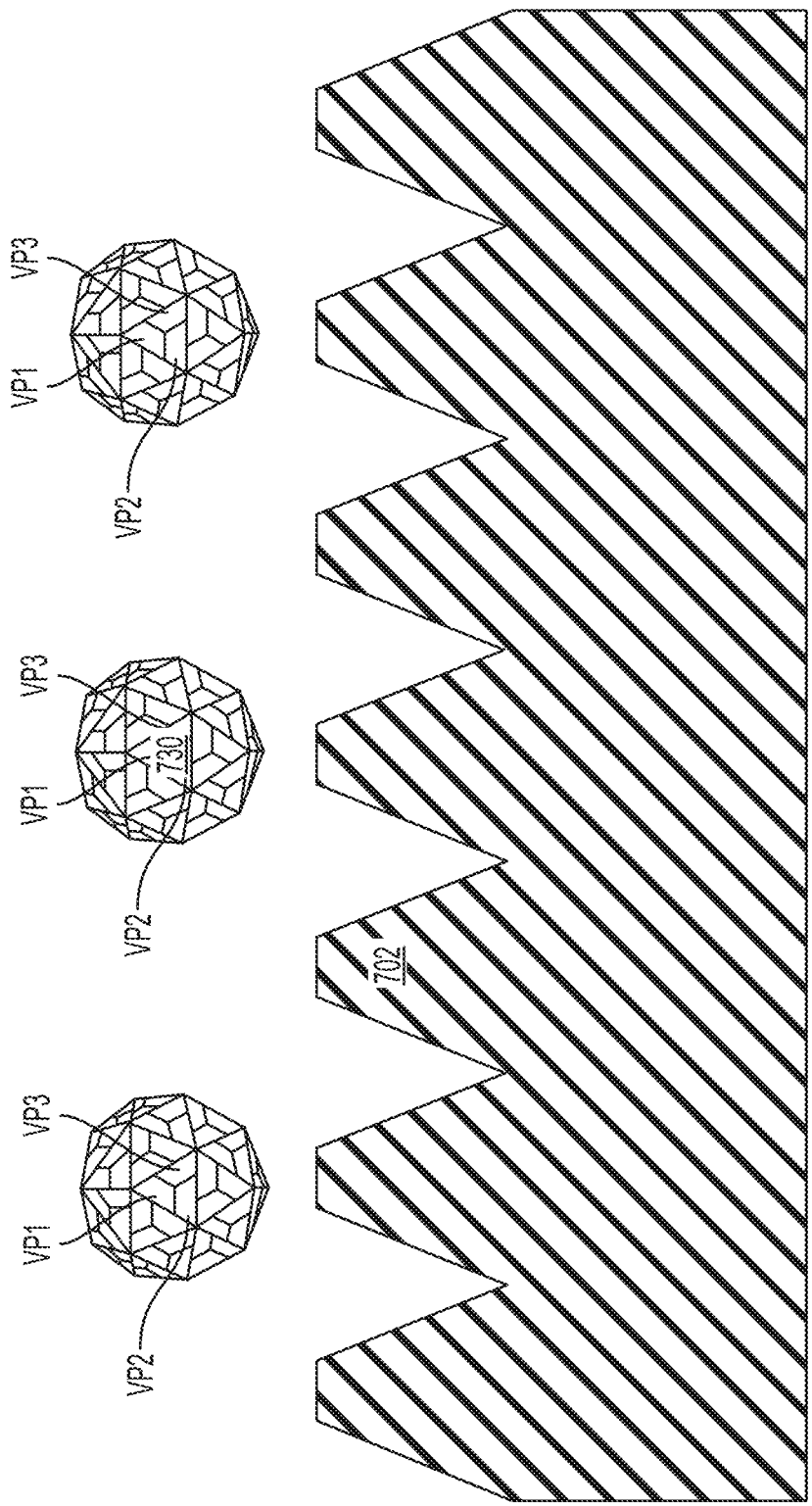
FIG. 7G is an array of blunt nanospikes.
Figure 7H:
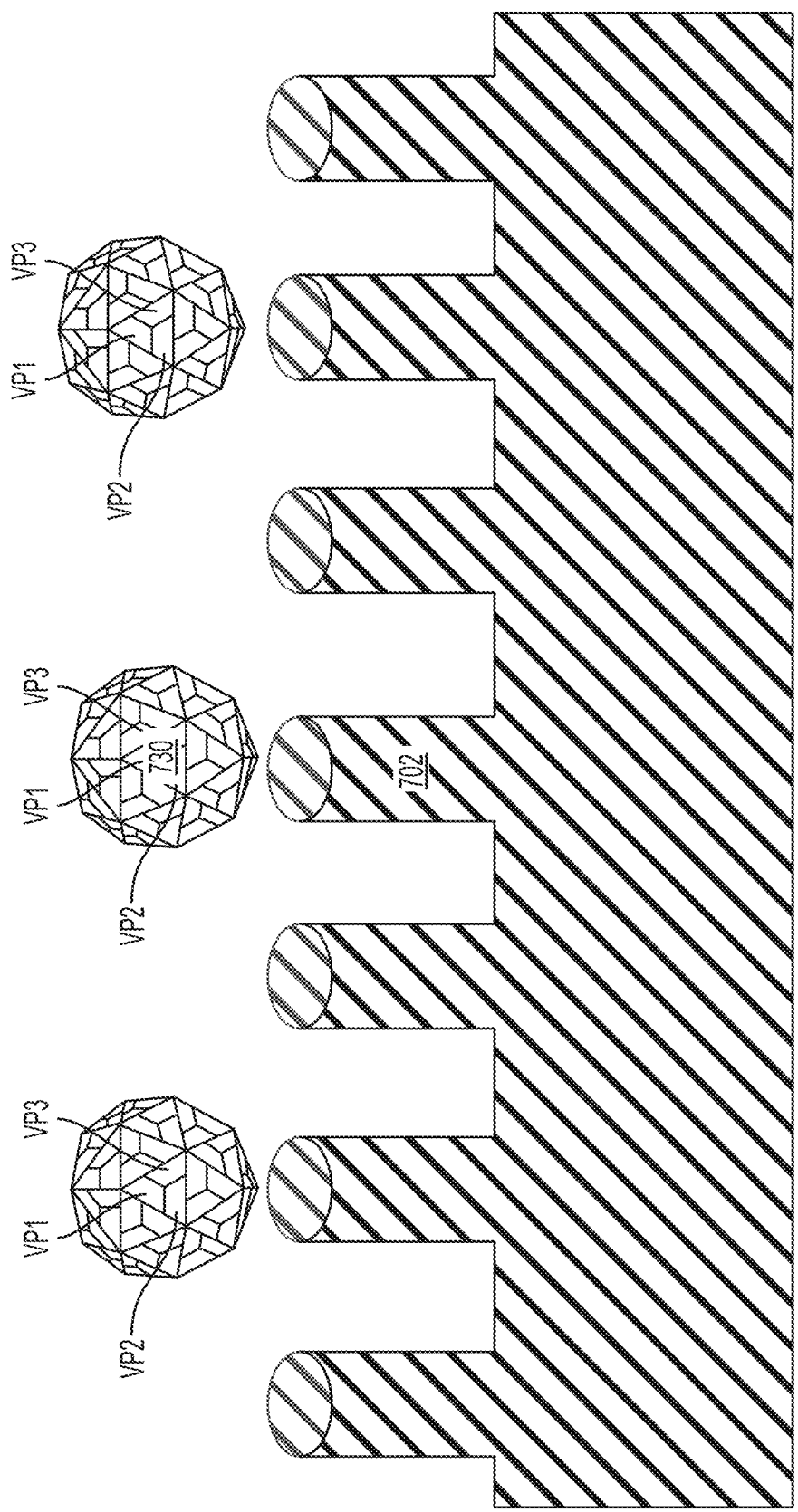
FIG. 7H is an array of rod-shaped nanospikes.

FIG. 7E is an array with nanospikes 702 having different sizes. The fractal pattern of spike sizes may be used for a broad range of microbe/virion size destruction, as shown for small microbe/virions 730 and large microbe/virions 731. The spacing 710 and depth 711 of the nanospikes 702 may also be altered, depending on the size of the target, as shown in FIG. 7F. Nanospikes 702 may have different shapes, and may be, for example, blunt nanospikes (FIG. 7G) or rod-like (cylindrical) nanospikes (FIG. 7H).

Figure 8A:
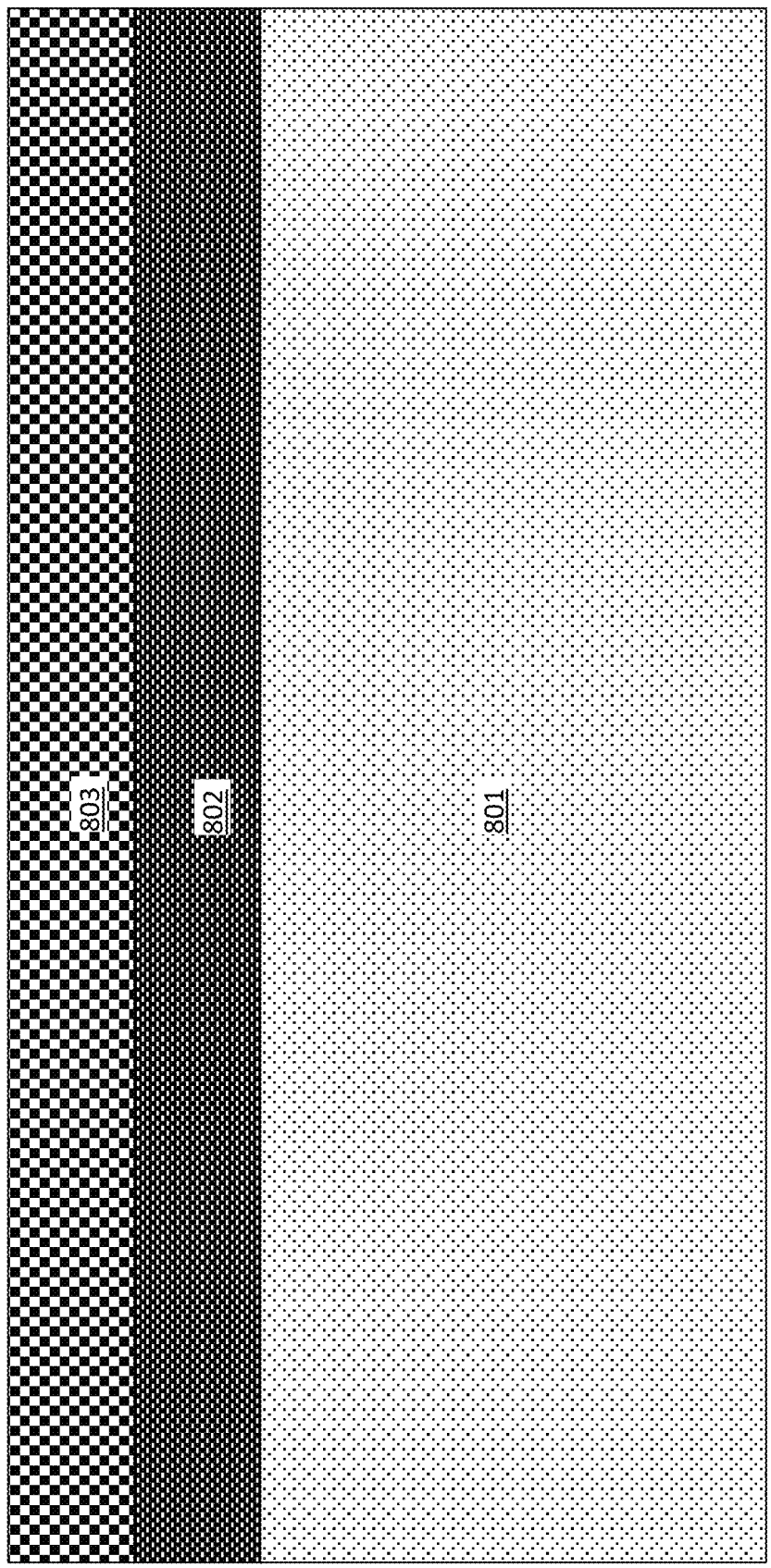

FIGS. 8A-8E illustrate methods of making nanoprotrusions (nanospikes) according to some embodiments. FIG. 8A is a cross-sectional side view of a photoresist 802 and hard mask 803 disposed on a substrate 801. The substrate 801 may include a semiconductor material. Non-limiting examples of semiconductor materials include Si (silicon, including polysilicon), strained Si, SiC (silicon carbide), Ge (germanium), SiGe (silicon germanium), SiGeC (silicon-germanium-carbon), Si alloys, Ge alloys, III-V materials (e.g., GaAs (gallium arsenide), InAs (indium arsenide), InP (indium phosphide), aluminum arsenide (AlAs)), or any combination thereof. Other non-limiting examples of semiconductor silicon-on-insulator (SOI) substrates with buried oxide (BOX) layers. The substrate 801 may be formed using, for example, chemical vapor deposition (CVD) (liquid phase (LP) or reduced pressure chemical vapor deposition (RP-CVD), vapor-phase epitaxy (VPE), molecular-beam epitaxy (MBE), liquid-phase epitaxy (LPE), metal organic chemical vapor deposition (MOCVD), or other suitable processes.

The hard mask 802 may be an insulating material, silicon nitride (SiN), SiOCN, SiBCN, or any combination thereof. The hard mask 802 may be formed using a deposition method, for example, a CVD method or a physical vapor deposition (PVD) method. The photoresist 803 may be, for example, a polymeric spin-on material or other polymeric material.

Figure 8B:
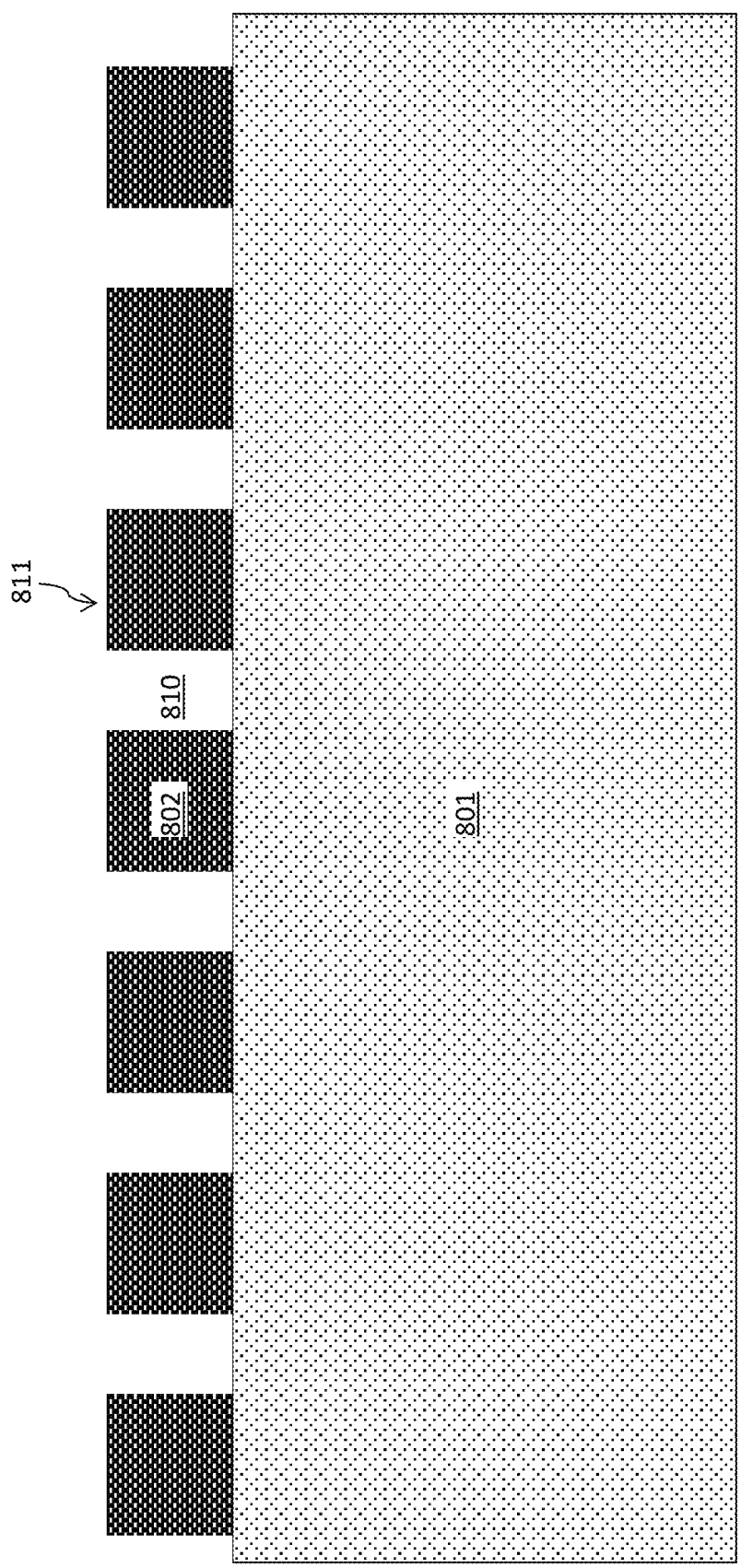
Figure 8C:
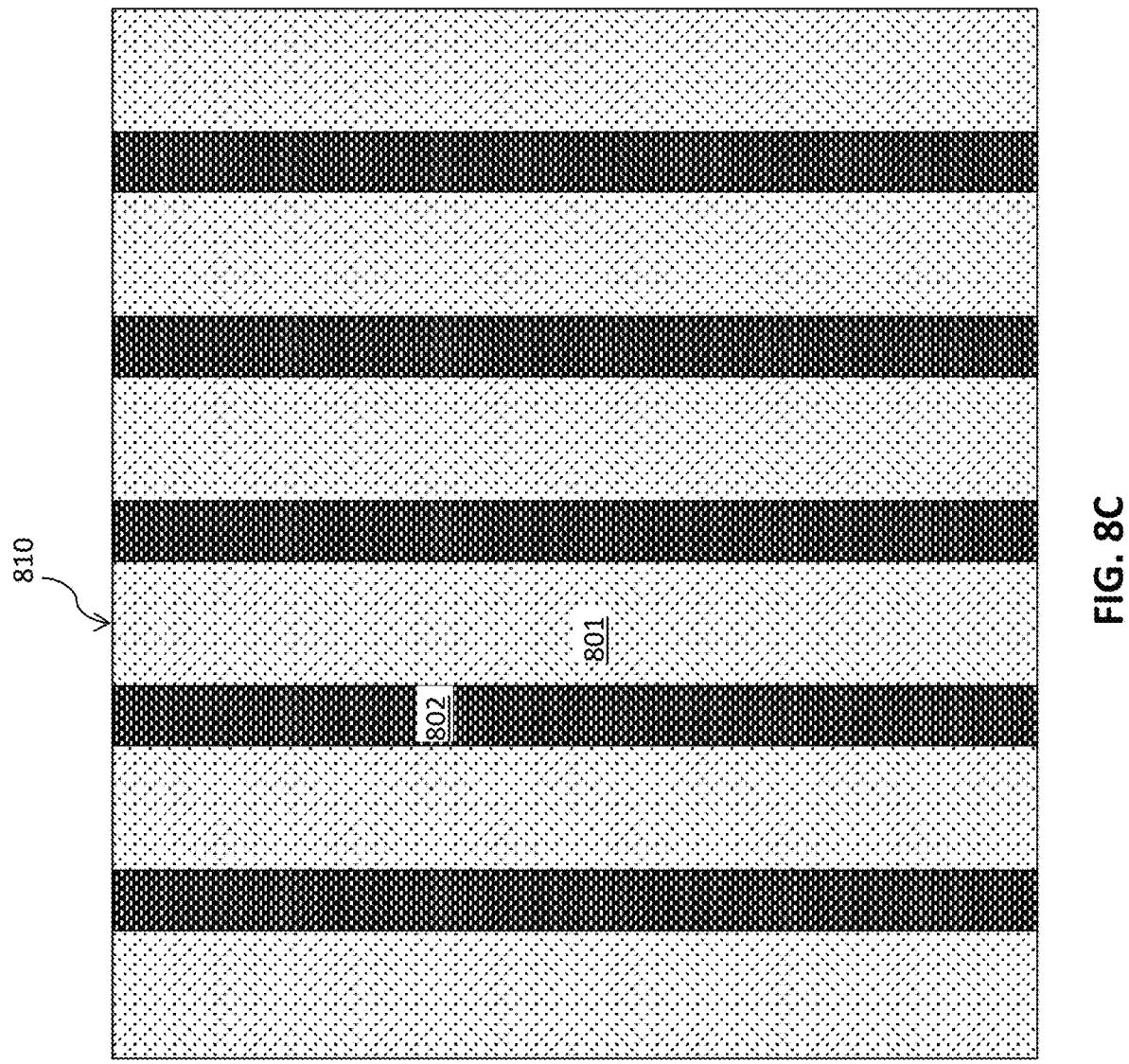

FIG. 8B is a cross-sectional side view after patterning the hard mask 802 and removing the photoresist 803. The photoresist is exposed to a desired pattern of radiation, and the exposed photoresist is developed with a resist developer to provide a patterned photoresist. At least one etch is employed to transfer the pattern from the patterned photoresist 803 into the hard mask 802 and to form gaps 810 (trenches) between hard mask pillars 811. The etch process may be a dry etch and/or wet etch process. After transferring the pattern, the patterned photoresist 803 is removed utilizing resist stripping processes, for example, ashing. FIG. 8C is a top view of FIG. 8B, showing that elongated "stripes" of the hard mask 802 are formed.

Figure 8D:
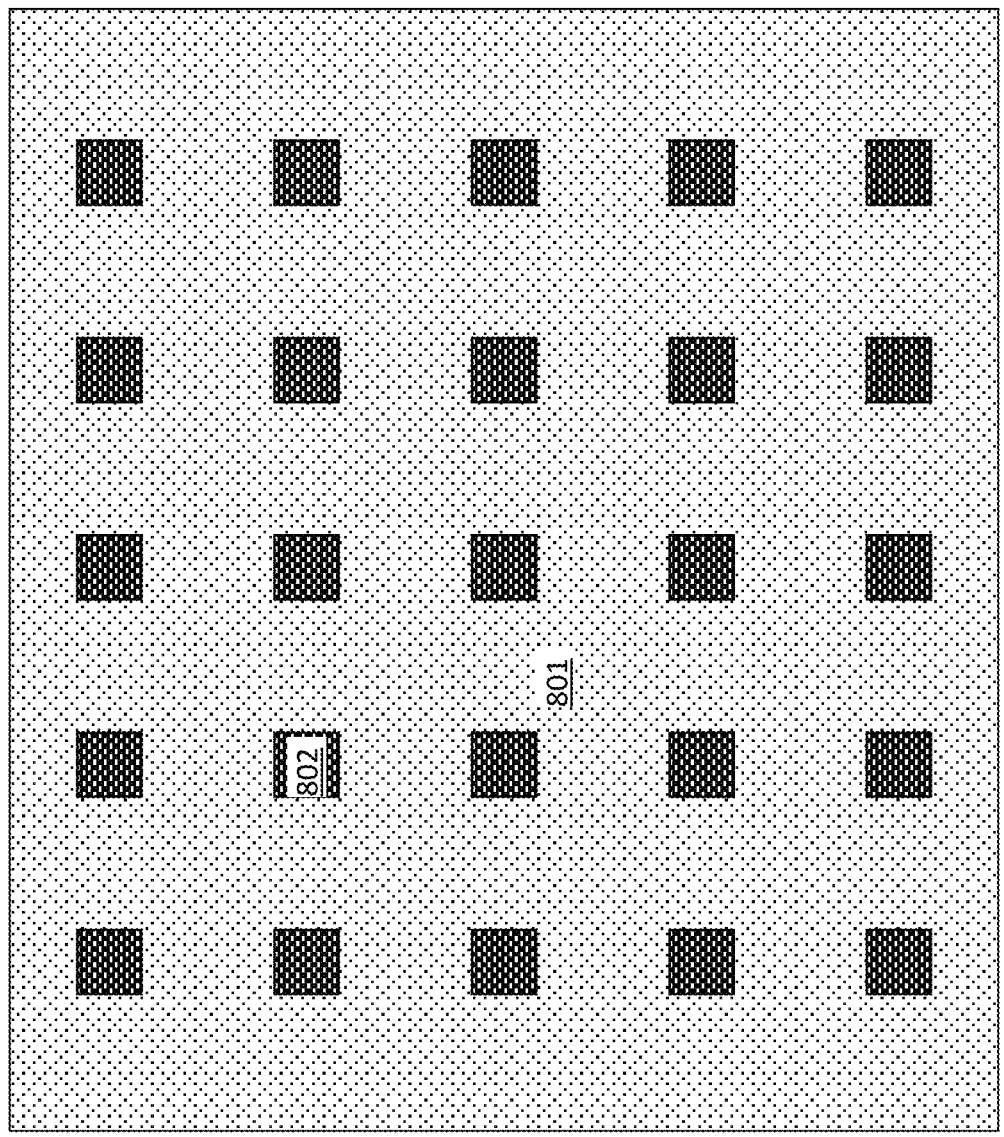

FIG. 8D is a cross-sectional side view after rotating the substrate 801 about 90 degrees and performing a second patterning and etch process, as described above for FIGS. 8A-8C. A second photoresist layer may be used, but is not necessary. A single photoresist may be used for the first and second patterning processed, for example, by a single resist double lithographic (or patterning) process. The second patterning process forms an array of individual scattered cube-like structures of the hard mask 802. Additional patterning (e.g., sidewall image transfer) and etching processes may be employed to form cube-like structures having smaller dimensions.

Figure 8E:
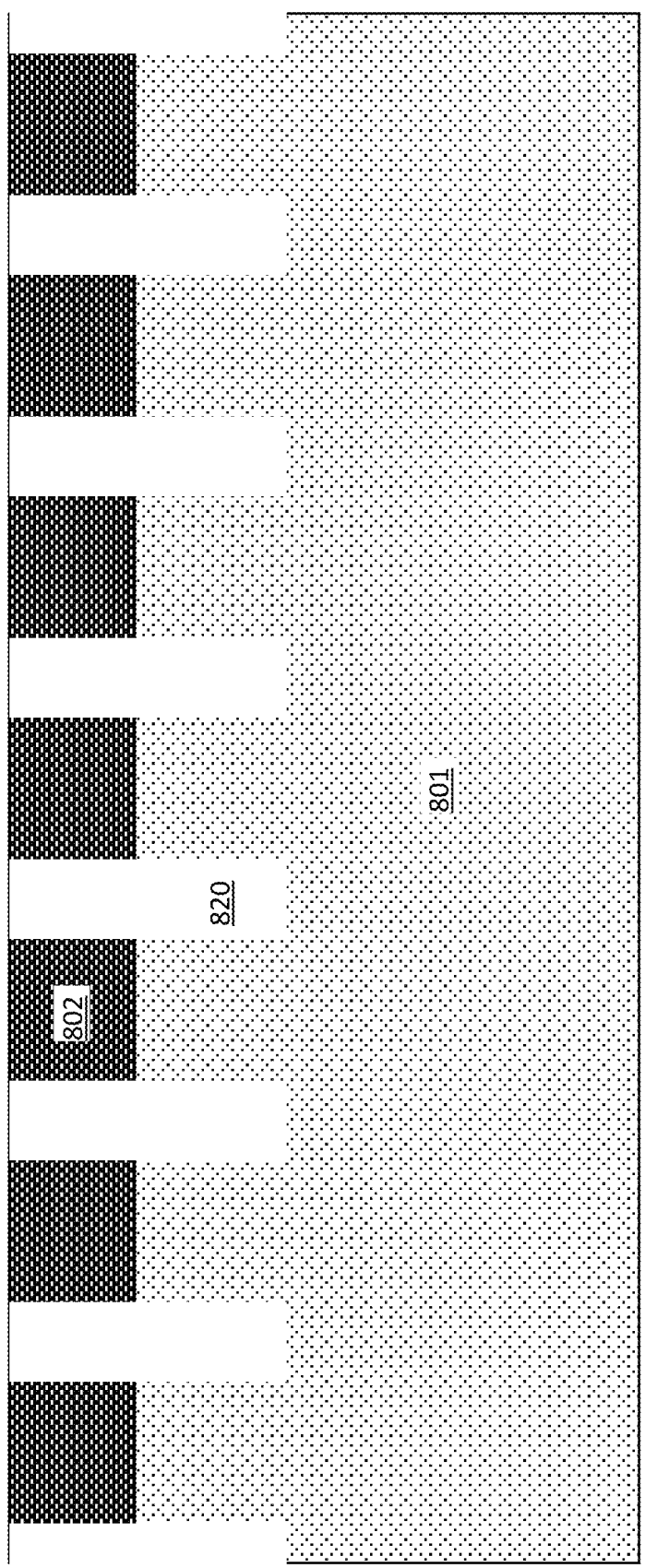

FIG. 8E is a cross-sectional side view after, optionally, recessing the substrate 801 to form trenches 820 beneath the hard mask 802. Recessing the substrate 801 creates will create a sharper tip in the final nanospike.

Figure 8F:
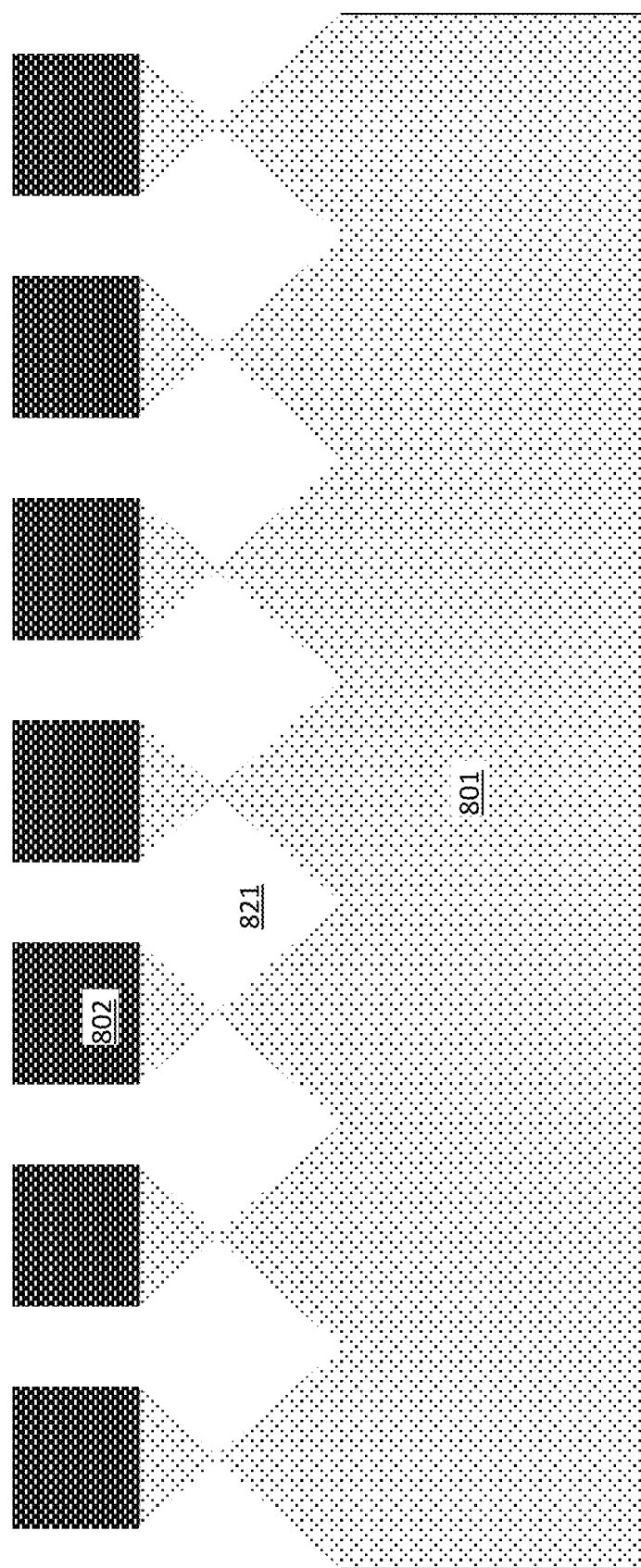
FIG. 8F is a cross-sectional side view after performing a crystallographic etch.

FIG. 8F is a cross-sectional side view after performing a crystallographic etch on the substrate trenches 820 to form inverse pyramid-shaped trenches 821. The crystallographic etch may be, for example, a crystallographic hydroxide etch. The hydroxide etch may include, for example, $NH_4OH$, KOH, tetramethylammonium hydroxide (TMAH), tetraethylammonium hydroxide (TEAH), or a combination thereof. The etch process may be a timed etch process or an over-etch process.

Figure 8G:
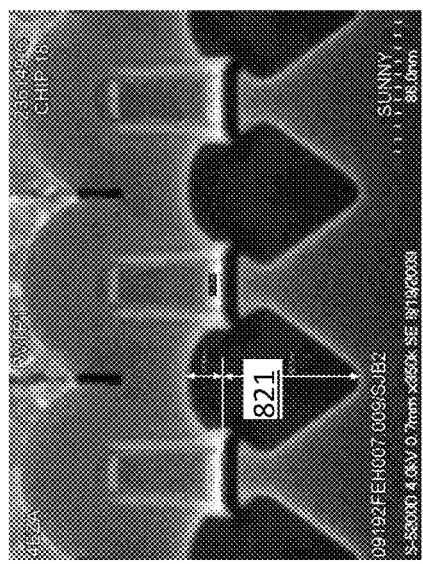
FIG. 8G is an electron micrograph image of a hydroxide etched substrate.

The inverse pyramid-shaped trenches 821 are formed due to different etch rates on different crystal planes in the substrate 801. FIG. 8G is an electron micrograph image of a hydroxide etched substrate having inverse pyramid-shaped trenches 821.

FIG. 8H is a cross-sectional side view after removing the remaining hard mask 802 material to form the array of nanospikes 840 in the substrate 801.

Figure 9:
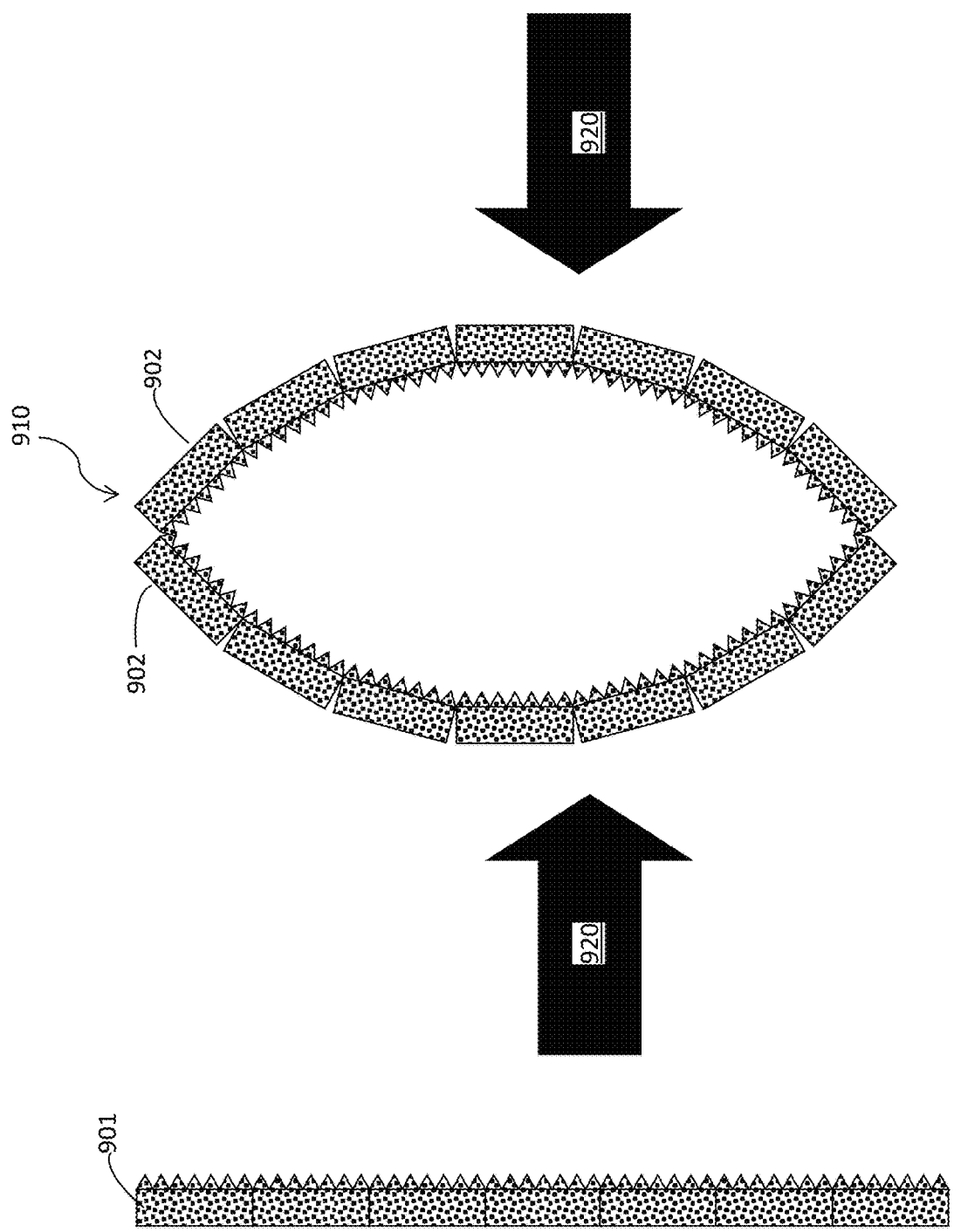

FIG. 9 illustrates a method for forming a flexible tube 910 with an array of nanospikes. The array of nanospikes extends into the center of the tube. A substrate sheet of nanospikes 901 is converted to a flexible film 902. The flexible film may be formed by, for example, performing a spalling process, for example, with nickel (Ni). The flexible film 902 may be inserted into another tube or capillary array to form a lining. Force, demonstrated by arrows 920, may be applied to constrict the passage between the flexible films 902 and bring more microbes/virions per unit volume into contact with the nanospikes. In other embodiments (not shown), the flexible film 902 may be rolled into the shape of a tube.

As described above, various embodiments provide methods for isolating, trapping, measuring, filtering, and attacking pathogens are described herein. The disclosed methods reduce the risk for pathogens developing antibiotic resistance. In some embodiments, a size-based trapping/filtering mechanism is described. In other embodiments, a spike-like envelope puncture mechanism is used.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, element components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

The diagrams depicted herein are just one example. There may be many variations to this diagram or the steps (or operations) described therein without departing from the spirit of the invention. For instance, the steps may be performed in a differing order or steps may be added, deleted or modified. All of these variations are considered a part of the claimed invention.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A device for isolating a microbe or a virion, comprising:
a silicon substrate;
an annealed layer of epitaxial silicon germanium arranged on the silicon substrate, the annealed layer of epitaxial silicon germanium comprising a roughened nanosurface comprising nanoscale germanium agglomerates; and a plurality of spaced trenches arranged in the roughened nanosurface between the nanoscale germanium agglomerates, the plurality of spaced trenches comprising a fractal pattern;

wherein each trench of the plurality of irregularly spaced trenches has dimensions such that the microbe or the virion is trapped within the trench.

2. The device of claim 1, wherein each trench has an average diameter in a range from about 70 to about 700 nanometers (nm).

3. The device of claim 1, wherein each trench further comprises a material having an affinity for the microbe or the virion.

4. The device of claim 1, further comprising a solution comprising the microbe or the virion disposed on the semiconductor substrate, the microbe or the virion being trapped within a trench of the plurality of trenches.

5. The device of claim 4, wherein the microbe or the virion is labeled with a fluorescent marker.

6. The device of claim 4, wherein the solution comprises different microbes or different virions.

\* \* \* \* \*